(12) United States Patent
Norrman et al.

(10) Patent No.: US 8,844,385 B2
(45) Date of Patent: Sep. 30, 2014

(54) DEVICE AND METHOD FOR SEPARATION OF PROTEINS AND OTHER BIOMOLECULES

(71) Applicant: GE Healthcare Bio-Sciences AB, Uppsala (SE)

(72) Inventors: Nils Norrman, Uppsala (SE); Ronnie Palmgren, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/857,646

(22) Filed: Apr. 5, 2013

(65) Prior Publication Data

US 2013/0220000 A1    Aug. 29, 2013

Related U.S. Application Data

(63) Continuation of application No. 12/597,968, filed as application No. PCT/SE2008/000341 on May 20, 2008, now Pat. No. 8,413,528.

(30) Foreign Application Priority Data

May 30, 2007 (SE) ........................... 0701316

(51) Int. Cl.
*B01L 3/02* (2006.01)
*G01N 30/84* (2006.01)
*G01N 1/22* (2006.01)
*G01N 30/06* (2006.01)
*B01L 3/00* (2006.01)
*G01N 30/00* (2006.01)
*G01N 30/60* (2006.01)

(52) U.S. Cl.
CPC .......... *G01N 30/84* (2013.01); *G01N 2030/062* (2013.01); *B01L 2300/0681* (2013.01); *B01L 3/0275* (2013.01); *B01L 3/508* (2013.01); *G01N 2030/009* (2013.01); *G01N 30/6065* (2013.01); *B01L 2400/0605* (2013.01); *B01L 2200/026* (2013.01)
USPC ................... 73/863.32; 73/863.23; 73/864.01

(58) Field of Classification Search
CPC .......... B01L 3/0275; B01L 2300/0681; B01L 3/0217; B01L 2400/0478; B01L 3/0279; B01L 3/0293; B01L 3/203; B01L 3/0206; B01L 3/0234; B01L 3/5025; G01N 35/10; G01N 35/1072; G01N 35/1074
USPC ............... 73/863.32, 863.31, 864.01, 864.17, 73/863.33, 864.41, 863.71, 863.73, 61.59, 73/61.68, 64.56, 864.72, 864.71, 864.15, 73/864.22, 864.14; 422/501, 524
See application file for complete search history.

(56) References Cited

U.S. PATENT DOCUMENTS 3,985,032 A * 10/1976 Avakian ...................... 73/863.25
4,744,955 A * 5/1988 Shapiro ...................... 134/100.1

(Continued)

FOREIGN PATENT DOCUMENTS

WO  WO 01/36935  5/2001
WO  WO 03/050231  6/2003

*Primary Examiner* — Daniel S Larkin
*Assistant Examiner* — Jamar Ray

(57) ABSTRACT

The present invention relates to a device and method for separation of proteins and other biomolecules. A preferred use is for sample preparation of crude as well as pre-fractionated samples. In a preferred embodiment, the device of the present invention is a pipette tip having dual channels, one for inlet of sample and one for outlet. The outlet, but not the inlet, channel is provided with sample separation media for separation of a desired biomolecule from a sample. The flow through the sample separation media is unidirectional.

5 Claims, 1 Drawing Sheet

(56) References Cited

U.S. PATENT DOCUMENTS 7,785,466 B1 * 8/2010 Smith ................... 210/321.75
2003/0183020 A1 10/2003 Kipke et al.
2006/0011548 A1 1/2006 Yin et al.
2006/0246501 A1 * 11/2006 Northrup ........................ 435/6

* cited by examiner

DEVICE AND METHOD FOR SEPARATION OF PROTEINS AND OTHER BIOMOLECULES

CROSS-REFERENCE TO RELATED APPLICATIONS

This application is a continuation application of U.S. patent application Ser. No. 12/597,968 filed Oct. 28, 2009, now U.S. Pat. No. 8,413,528, which is a filing under 35 U.S.C. §371 and claims priority to international patent application number PCT/SE2008/000341 filed May 20, 2008, published on Dec. 4, 2008, as WO 2008/147281, which claims priority to patent application number 0701316-2 filed in Sweden on May 30, 2007.

FIELD OF THE INVENTION

The present invention relates to a device and method for separation of proteins and other biomolecules. A preferred use is for sample preparation of crude as well as pre-fractionated samples. In a preferred embodiment, the device of the present invention is a pipette tip having dual channels, one for inlet of sample and one for outlet. The outlet, but not the inlet, channel is provided with sample separation media for separation of a desired biomolecule from a sample.

BACKGROUND OF THE INVENTION

It is often desired to separate target molecules from complex mixtures, such as body fluids. The target molecule may be any biomolecule present in such a fluid, for example protein, peptide, nucleic acid and carbohydrates. Most often this requires pre-fractionation of the sample or some kind of sample preparation. Sample preparation is conventionally performed by chromatography or electrophoresis.

For chromatography on columns the sample flow, in binding or elution mode, is in one direction, i.e. the sample is usually loaded on the top of the column and collected at the bottom of the column.

Another way of achieving sample preparation is by using pipette tips filled with separation media. In prior art pipette tips for sample preparation, the sample is drawn into the pipette tip and is allowed to react with the separation media in the tip. The sample is drawn into the same channel of the pipette tip as it is later expelled from the pipette tip when the desired contact with the separation media has occurred. Thus, the flow of sample in the pipette tip is in two opposite directions, first into the tip and then out of the tip. This has a number of drawbacks, for example the separation media will be contaminated with sample constituents already when the sample is moving into the pipette which impairs the separation of the desired target molecules when the sample is flowing out of the tip and collected. Furthermore, the separation media in the pipette tip may be clogged with sample proteins and other molecules on their way up in the tip which will make it impossible to elute any proteins of interest in the outflow from the tip.

Therefore, there is a need within the sample preparation area to provide a convenient device which avoids the above drawbacks but still provides the desired separation.

SUMMARY OF THE INVENTION

The present inventors provide a separation device, preferably in the form of a pipette tip comprising a separate inlet and outlet. The device provides for uptake of sample in the inlet which does not come into contact with sample separation media present in the outlet. The sample separation media is only located in the outlet of the device. The sample is contacted with and eluted from the sample separation media in the outlet in regular manner. This increases reproducibility and decreases contamination problems.

In a first aspect, the invention relates to a sample separation device for separation of a biological sample, comprising and inlet channel and an outlet channel, wherein only the outlet channel is provided with sample separation media, and wherein the sample is drawn into the inlet channel and only comes in contact with the sample preparation media in the outlet when the sample is expelled from the device.

Preferably, the sample preparation device comprises a pipette tip with separated inlet and outlet channels. A purpose of having two separate channels for inlet and outlet, respectively, is to prevent premature contact between the sample constituents and the separation matrix in the outlet. Another purpose is to enable unidirectional flow in the inlet and outlet channel, respectively. Preferably, the inlet and/or the outlet channels are provided with back valves for securing unidirectional flow.

The pipette tip may be manually or automatically arranged on a pipette. Several pipette tips may be used in a pipette manifold. The procedure may be performed manually or automatically.

In one embodiment, the inlet and outlet channels are arranged substantially in parallel.

In a further embodiment, the inlet channel is arranged centrically in the outlet channel.

In yet a further embodiment, the outlet channel is arranged centrically in the inlet channel.

Only the outlet channel, and not the inlet channel, is provided with separation media.

Preferably, the inlet and outlet channels are arranged physically separated from each other.

The separation media in the outlet channel may be any separation media that separates biomolecules from each other. Examples of separation media are size exclusion media, ion exchange media, IMAC (immobilised metal affinity chromatography) media, affinity media, HIC (hydrophobic interaction) media, RPC (reversed phase chromatography) media or any combination thereof. Other examples of separation media are monoliths, membranes, filters and hydrogels, which may be used in the outlet of a device according to the invention and which requires unidirectional flow of sample.

The device according to the invention may be used for any type of separation with the above media. It may be separation of sample components from other sample constituents, such as other biomolecules or cellular components. Another option is to use the device for more general purposes, such as desalting a sample. In this case the separation media may be a size exclusion media or a filter.

Preferably, the inlet channel is provided with a back valve at the upper end thereof. The back-valve function of the inlet for one-way flow can be constructed in different ways but the main purpose is to prevent the sample from flowing out of the device in the same channel as it entered the device. In some embodiments, also the outlet channels may be provided with a back valve as will be described more closely below.

Several embodiments are possible, for example a) double pipette tips wherein you soak in one tip (i.e the inlet channel) and elute through the other tip (i.e. outlet channel) which contains the matrix b) a capillary as inlet channel in the middle of a wider outlet channel; and c) a monolith which is not bond to the wall which allows the solution to pass through on the outside thereof.

In yet a further embodiment, the inlet channel is physically arranged outside the pipette tip, for example as a thin tube adhered to the outside of a pipette tip which will be provided with separation media and serve as outlet channel.

Preferably, the inlet channel is narrower than the outlet channel to provide more space for the outlet channel in which the sample preparation is performed.

The sample preparation media is selected from chromatography beads, hydrogels, monoliths, membranes, filters or a combination thereof.

In a second aspect, the invention relates to a method for sample preparation of a biological sample, comprising the following steps a) drawing sample into an inlet channel of a device as described above; b) contacting the sample with separation media in an outlet channel; and c) expelling sample from the outlet channel, wherein the sample only comes in contact with the sample separation media when the sample is expelled from the device.

DETAILED DESCRIPTION OF THE INVENTION

The invention will now be described in connection with some non-limiting examples with referral to the accompanying drawings. It is to be understood that the drawings only are examples of the sample preparation device of the invention which is only to be limited by the scope of the appended claims.

EXAMPLES

Below the present invention will be disclosed by way of examples, which are intended solely for illustrative purposes and should not be construed as limiting the present invention as defined in the appended claims. All references mentioned below or elsewhere in the present application are hereby included by reference.

Example 1

Figure 1A:
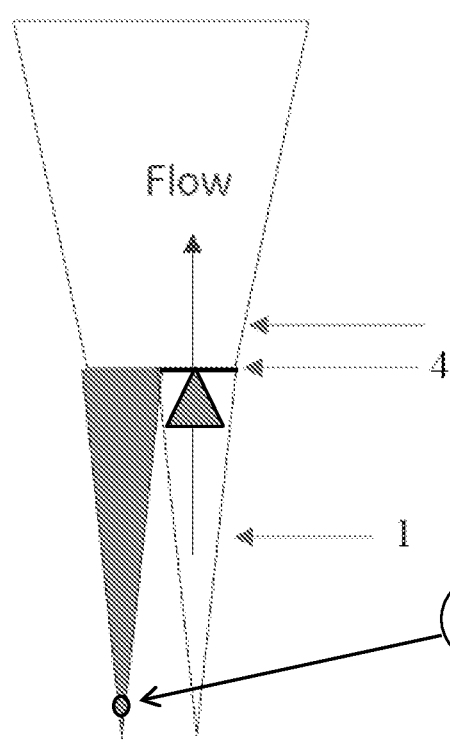
FIG. 1a and FIG. 1b are schematic views of a pipette tip for sample preparation according to the present invention.
Figure 1B:
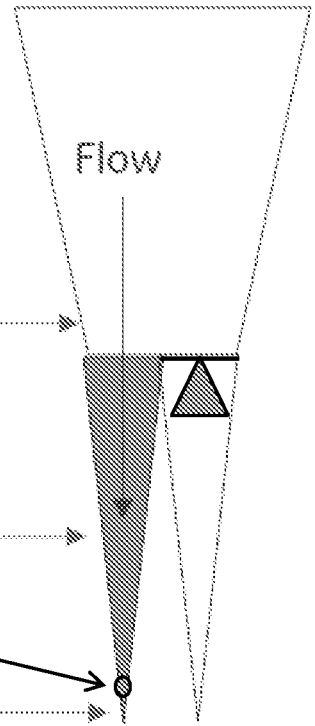

This example refers to FIG. 1a and FIG. 1b. A pipette tip is shown with dual tips, 1 and 2. The tip 1 functions as inlet for incoming flow of sample, for example serum (FIG. 1a). When the sample has been drawn into the upper compartment 3 of the pipette tip, then it is expelled through the second tip 2, which functions as an outlet for the sample. The shaded area in outlet 2 represents a separation matrix. To prevent sample from enter the second pipette tip with the incoming flow and prevent sample to enter the same way it entered the tip during elution, two back valves are provided one at the lower end 5 of the second tip 2 and one at the upper end 4 of inlet 1, which only allows flow in downwards direction as shown by the arrow in FIG. 1b.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A sample separation pipette tip, comprising an inlet channel (1) and an outlet channel (2), which outlet channel is provided with sample separation media, wherein the sample is drawn into the inlet channel and only comes in contact with the sample separation media in the outlet channel when the sample is expelled from the pipette tip, wherein the pipette tip has two tips one for each separate inlet and outlet channel that are arranged substantially in parallel.

2. The sample separation pipette tip of claim 1, wherein the inlet channel is provided with a back valve.

3. The sample separation pipette tip of claim 1, wherein the outlet channel is provided with a back valve.

4. The sample separation pipette tip of claim 1, wherein the separation media is selected from chromatography beads, hydrogels, monoliths, membranes, filters or a combination thereof.

5. A method for sample separation of a biological sample, comprising the following steps:
   a) drawing the sample into an inlet channel (1) of the pipette tip of claim 1;
   b) contacting the sample with sample separation media in an outlet channel (2); and
   c) expelling the sample from the outlet channel, wherein the sample only comes in contact with the sample separation media when the sample is expelled from the pipette tip.

* * * * *